United States Patent
Cumbie

(10) Patent No.: US 7,494,502 B2
(45) Date of Patent: *Feb. 24, 2009

(54) ALTERATION OF THE SKIN AND NAIL FOR THE PREVENTION AND TREATMENT OF SKIN AND NAIL INFECTIONS

(75) Inventor: William E. Cumbie, Yorktown, VA (US)

(73) Assignee: Keraderm, LLC, Hampton, VA (US)

( * ) Notice: Subject to any disclaimer, the term of this patent is extended or adjusted under 35 U.S.C. 154(b) by 266 days.

This patent is subject to a terminal disclaimer.

(21) Appl. No.: 11/185,791

(22) Filed: Jul. 21, 2005

(65) Prior Publication Data

US 2006/0173515 A1    Aug. 3, 2006

Related U.S. Application Data

(63) Continuation-in-part of application No. 11/154,707, filed on Jun. 17, 2005, which is a continuation-in-part of application No. 10/215,834, filed on Aug. 9, 2002, now Pat. No. 6,960,201.

(60) Provisional application No. 60/649,316, filed on Feb. 2, 2005, provisional application No. 60/355,088, filed on Feb. 11, 2002.

(51) Int. Cl.
*A61N 5/06* (2006.01)

(52) U.S. Cl. .............. 607/88; 607/89; 607/94; 606/3; 606/9; 128/898

(58) Field of Classification Search ............. 607/88–95; 606/3–31, 131; 128/898
See application file for complete search history.

(56) References Cited

U.S. PATENT DOCUMENTS

| | | | |
|---|---|---|---|
| 1,183,949 A | 5/1916 | Burdick | |
| 1,510,080 A | 9/1924 | Murphy | |
| 1,702,028 A | 2/1929 | Blanchard | |
| 1,856,969 A | 5/1932 | Reiter et al. | |
| 2,165,449 A | 7/1939 | Budd | |
| 3,986,513 A | 10/1976 | Stuhl | |
| 4,246,905 A | 1/1981 | Corth | |
| 4,298,005 A | 11/1981 | Mutzhas | |
| 4,558,700 A | 12/1985 | Mutzhas | |
| 4,871,559 A | 10/1989 | Dunn et al. | |
| 4,909,254 A | 3/1990 | Wilkinson | |
| 4,910,942 A | 3/1990 | Dunn et al. | |
| 4,930,504 A | 6/1990 | Diamantopoulos | |
| 4,951,663 A | 8/1990 | L'Esperance, Jr. | |
| 5,034,235 A | 7/1991 | Dunn et al. | |
| 5,344,433 A | 9/1994 | Talmore | |
| 5,871,522 A | 2/1999 | Sentilles | |
| 5,900,211 A | 5/1999 | Dunn | |
| 5,947,956 A | 9/1999 | Karell | |
| 5,949,956 A | 9/1999 | Karell | |
| 5,968,986 A | 10/1999 | Dyer | |
| 6,022,549 A | 2/2000 | Dyer | |
| 6,042,603 A | 3/2000 | Fisher et al. | |
| 6,053,180 A | 4/2000 | Kwan | |
| 6,090,788 A * | 7/2000 | Lurie | 514/23 |
| 6,129,893 A * | 10/2000 | Bolton et al. | 422/23 |
| 6,165,170 A | 12/2000 | Wynne et al. | |
| 6,174,325 B1 | 1/2001 | Eckhouse | |
| 6,183,773 B1 | 2/2001 | Anderson | |
| 6,254,625 B1 | 7/2001 | Rosenthal et al. | |
| 6,264,836 B1 | 7/2001 | Lantis | |
| 6,264,888 B1 | 7/2001 | Palestro | |
| 6,283,986 B1 | 9/2001 | Johnson | |
| 6,379,376 B1 | 4/2002 | Lubart | |
| 6,436,127 B1 | 8/2002 | Anderson et al. | |
| 6,464,625 B2 * | 10/2002 | Ganz | 600/3 |
| 6,565,803 B1 | 5/2003 | Bolton | |
| 6,663,659 B2 * | 12/2003 | McDaniel | 607/88 |
| 6,835,202 B2 | 12/2004 | Harth | |
| 6,908,881 B1 | 6/2005 | Sugihara | |
| 6,960,201 B2 * | 11/2005 | Cumbie | 606/9 |
| 6,960,210 B2 | 11/2005 | Cumbie | |

(Continued)

FOREIGN PATENT DOCUMENTS

WO    WO 99/17668    4/1999

(Continued)

OTHER PUBLICATIONS

Rudiger Hell, 'Sulfer Rich Proteins Involved in Stress Resistance'. 25 pages. The Heidelburg Institute of Plant Sciences, Univ. of Heidelburg, Germany.

Osbourne, 'Antimicrobial Phytoprotectants and Fungal Pathogens: A Commentary', 1999. Fungal Genetics and Biology, pp. 163-168. Salisbury Lab, Norwich, England.

(Continued)

*Primary Examiner*—Ahmed M Farah
(74) *Attorney, Agent, or Firm*—Merek, Blackmon & Voorhees, LLC

(57) ABSTRACT

The method of prevention and treatment of microbial infections that occur on, or just below, the skin and nails of a person consisting of applying a means to inactivate the microbes thus rendering them harmless. The treatment consists of applying a means which alters the skin or nail so that the skin or nail will either no longer serve as a food source, will be inhibitory to the organism, will be toxic to the organism, or will be altered in a manner that makes it more responsive to treatment of infections.

87 Claims, 1 Drawing Sheet

U.S. PATENT DOCUMENTS

| | | | |
|---|---|---|---|
| 6,984,228 B2 | 1/2006 | Anderson et al. | |
| 7,177,695 B2* | 2/2007 | Moran | 607/50 |
| 7,306,620 B2 | 12/2007 | Cumbie | |
| 2002/0083535 A1 | 7/2002 | Fraden | |
| 2002/0161418 A1 | 10/2002 | Wilkens | |
| 2002/0183811 A1 | 12/2002 | Irwin | |
| 2003/0023284 A1 | 1/2003 | Garstein | |
| 2003/0027186 A1 | 2/2003 | Pierce | |
| 2003/0157073 A1* | 8/2003 | Peritt et al. | 424/93.21 |
| 2004/0236267 A1 | 11/2004 | Pierce | |
| 2005/0019256 A1 | 1/2005 | Dobkine et al. | |
| 2005/0019258 A1 | 1/2005 | Dobkine et al. | |
| 2005/0079096 A1 | 4/2005 | Brown-Skrobot et al. | |
| 2005/0242301 A1 | 11/2005 | Pierce | |
| 2005/0256552 A1 | 11/2005 | White | |
| 2005/0256553 A1 | 11/2005 | Strisower | |
| 2006/0004425 A1* | 1/2006 | Cumbie | 607/86 |
| 2006/0079948 A1 | 4/2006 | Dawson | |
| 2006/0173515 A1 | 8/2006 | Cumbie | |
| 2006/0212098 A1 | 9/2006 | Demetriou | |
| 2006/0241729 A1 | 10/2006 | Dawson | |

FOREIGN PATENT DOCUMENTS

| | | |
|---|---|---|
| WO | WO 03/068310 A3 | 8/2003 |

OTHER PUBLICATIONS

National Biological Corporation, Derma-Wand Advertisement, 1999, 2 pages.
Wekhof, Alexander, "Disenfection with Flash Lamps", May 2000, pp. 264-276.
Wekhof, Alexander, "Pulsed UV Disintegration (PUVD): a new sterilisation mechanism for packaging and borad medical hspital applications.", May 2000, pp. 264-276.
Dawson, Timothy, Appl. 10/908,059, Filed Apr. 26, 2005, amendment filed Mar. 27, 2007, pp. 1-12.
Moller, et al. 'How Finsen's Lamp Cured Lupus Vulgaris',2005. pp. 118-124, Photodermatology, Photoimmunology, and Photomedicine. Pub. by Blackwell Muskgaard, Copenhagen, Den.
Russell, "Ultra-Violet Radiation and Actinotherapy", 1933. Cover, TOC and pp. 260-305 and 416-447. Pub. by E&S Livingstone, Edinburgh, Scotland.
Clayton, 'Electrotherapy and Actinotherapy', 1952. Cover, TOC, and pp. 312-362 and 410-429 Pub. by Baillere, Tindall, and Cox, London, England.
United Nations—World Health Organization, 'Summary of Env. Health Criteria 160', Undated. 8 pages. Pub. by WHO, Geneva, Switzerland, 1994.
U.S. Environmental Protection Agency, 'Manual of Alternative Disinfection', 1999. Chapter 8 (pp. 8-1 to 8-25). Published by USEPA, Washington D.C.
United Nation—World Health Organization, 'Env. Health Criteria 160', 1994. Table of Contents and Chapter 6 (Celluar and Molecular Studies). Pub. by WHO, Geneva, Switzerland.
FDA,'Kinetics of Microbial Inactivation for Alternative Food Processing Technologies', 2000. 8 page summary. Pub. by FDA, Washington, DC.
Beckett, 'Modern Actinotherapy', 1955. Cover, TOC, and pp. 78-111. Published by William Helnemann, London, England.
Fluharty, et al. 'The Discovery and Subsequent Research of Cryptosporidium Inactivation', Undated. 6 pages. Published by Calgon Corporation, Pittsburgh, PA. Mar. 2002.
Moss and Davies. 'Interrelationship of Repair Mechanisms in Ultraviolet Irradiated Escherlchia coli', Oct. 1974. Journal of Bacteriology pp. 15-23. Pub. Am. Soc. of Microbio.
Smith. 'Scientific History of Kendric Smith', Undated. 39 pages. Published on the Internet, 2002.
Government of India, First Examination Report, p. 1-2, India, Jul. 4, 2007.
European Patent Office, Supplementary European Search Report, p. 1-4, Munich, Germany, Nov. 14, 2005.
Beckett, Raymond H., Modern Actinotherapy, p. 1-161, William Heinermann-Medical Books, Ltd., London, England, 1955.
Clayton, E.B., Electrotherapy and Actinotherapy, p. 1-452, Bailliere, Tindal and Cox, London, England, 1952.
Russell, Eleanor H. et al., Ultra-Violet Radiation and Actinotherapy. p. 1-648, E & S Livingstone, Edinburgh, Scottland, 1933.
Ahmed, R.G., Damage Patterns as Function of Various Types of Radiations. Medical Journal of Islamic World Academy of Sciences 15:4, 135-147, 2005.
El-Awady et al., Heat effects on DNA repair after ionising rdiation: hypertherma comonly increases the number of non-repaired double-strand breaks and structural rearrangements. Nucleic Acids Research, vol. 29, No. 9, p. 196-1966, Oxford University, 2001.
Ennis, William J. et al., A biochemical approach to wound healing through the use of modalities, Clinics in Dermatology (2007) 25, 63-72, 2007.
Foa, Kinetics of Microbial Inactivation for Alt. Food Processing Tech.-Pulsed LIght Tech., Jun. 2, 2000, 9 pgs. Wash. D.C.
EPA, the EPA Guidance Manual on Alt. Disinfectants, Chapter 8, Apr.-1999, 43 pgs., Wash. D.C.
The Health Physics Society, Ultraviolet Radiation and the Public Health, Jul. 1998, 2 pgs, McLean, VA.
American Ultraviolet Company, Determining UV Intensity and UV Inactivation Charts, No. Date, 5 pgs., Murray Hill, NJ. . Reprinted by Applicant at least as early as Oct. 2002.
Atlantic Ultraviolet Company, UV Inactivation Charts, 2001, 2 pgs. Hauppauge, NY.
World Health Org., Health and Environmental Effects of UV Rad., 1995, 8 pages, New York, NY, Ref. Fig. 3.
Conner-Kerr, Effects of UVC on a Perineal Inf. by C. Albicans in a Female With Type 2 Diabetes., After Dec. 2001, Abstract for Poster Session at the 15.sup.th Annual Symposium on Advanced Wound Care (Apr. 2002).

* cited by examiner

ALTERATION OF THE SKIN AND NAIL FOR THE PREVENTION AND TREATMENT OF SKIN AND NAIL INFECTIONS

CROSS-REFERENCE TO RELATED APPLICATIONS

This application claims the benefit of U.S. Provisional Application Ser. No. 60/649,316 filed Feb. 2, 2005, which is incorporated herein by reference. This application is also a continuation in part of U.S. Application Ser. No. 11/154,707, filed Jun. 17, 2005, published on Jan. 5, 2006, as U.S. Patent Publication No. 2006-0004425, which is a continuation in part of U.S. Application Ser. No. 10/215,834 filed Aug. 9, 2002, now U.S. Pat. No. 6,960,201, issued on Nov. 1, 2005, which claims the benefit of U.S. Provisional Application 60/355,088 filed Feb. 11, 2002, each of which application is incorporated herein by reference.

BACKGROUND

Field of Invention

Nail infections are a particularly significant problem in the general population, affecting an estimated 5% to 15% of the overall population. This percentage is significantly higher in the elderly age group and among athletes and other individuals who have high moisture in the area of their feet. It is estimated that approximately 25% of those over 65 suffer from nail infections.

Nail infections are often caused by fungus and this type of infection is termed onychomycosis. Currently, the preferred method for the prevention and treatment of skin and nail infections relies on application of topical medications or ingestion of medications. These medications are used to treat an existing infection, not for the prevention of an infection. Cost of treatment for nail infections by using medication can be between $600 and $1200 per course of treatment and can last three to six months. This is the amount of time it takes the medication to be incorporated into the nails. Another one to six months is then required for the nail to become free of infection. These medications also have a low cure rate with the efficacious having a total cure rate of less than 40%. In addition to the high costs and low cure rates, oral medications for nail infections have serious side effects including heart and liver problems, loss of taste for a year or more, and at times they can cause death.

Topically applied medications are safer than oral medications but have a much lower cure rate. Most topically applied medications for nail infections have cure rates of less than 15%. This is because these medications have difficulty in penetrating the nails effectively. While topically applied medications for skin infections are more efficacious even these medications have drawbacks including side effects such as rashes and other allergic reactions.

No effective method has been developed to prevent or treat skin and nail infections by changing the composition of the skin or nail without the use of oral medications or the application of topical medications.

SUMMARY OF INVENTION

The invention, a method to prevent and treat skin and nail infections, alters the composition of the skin or nail so that the skin or nail is either changed so that is will no longer sustain an infectious organism or so that it becomes inhibitory or toxic to an infectious organism.

Alteration of the skin or nail may be accomplished by a variety of means such as the use of electromagnetic radiation, application of heat, or other mechanical means. The alteration of the skin or nails may also be accomplished by the application of a compound which may by itself not be an antimicrobial compound (i.e. it may not be an antibiotic) but which when applied serves to inhibit the infectious organism.

The means used to alter the skin or nail may also change the skin or nail so that it is no longer available to the organism as a food source. When the skin or nail is altered in this manner an infectious organism cannot survive since it loses its source of food.

The means used to alter the skin or nail may also change the skin or nail so that it is inhibitory to an organism. This is different than the use of a means to directly inhibit the organism since it is the alteration of the skin or nails which inhibits the organism, not the means itself that inhibits the organism.

The means used to alter the skin or nail may also change the skin or nail so that it is toxic to an organism. This is different than the use of a means which is directly toxic to the organism since it is the alteration of the skin or nails which is toxic the organism, not the means itself that is toxic to the organism.

The means used to alter skin or nail may also change the skin or nail so that its characteristics are changes in a manner that make them more responsive to treatment of skin and nail infections. For example this may mean that the nail becomes more permeable and thus antibiotics may more easily transit the nails to the site of an infection.

BACKGROUND INFORMATION ON SKIN AND NAILS

Figure 1:
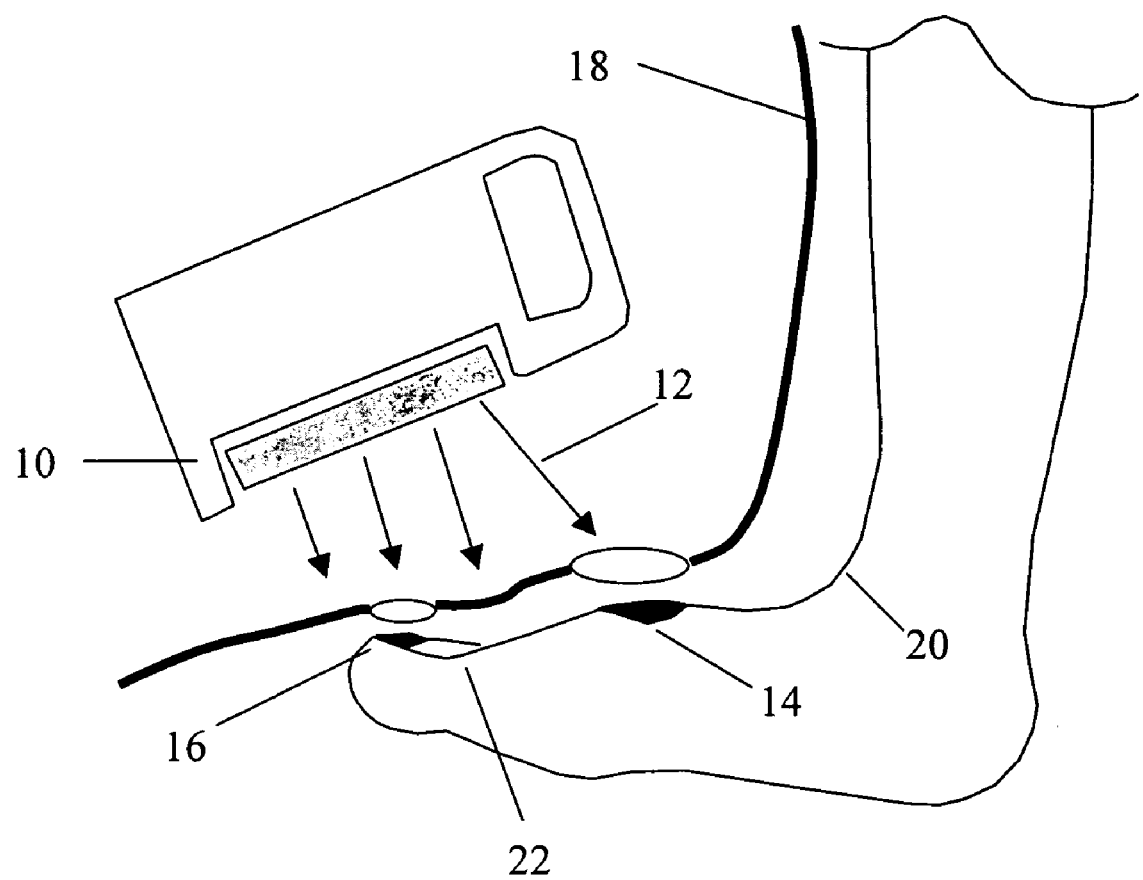
FIG. 1 is a schematic diagram of the method of treatment embodied by the invention.

The skin is the largest organ of the body and its main barrier against infection and damage. It is composed of an upper layer called the epidermis and the layer residing underneath called the dermis. The epidermis is generally renewed every 15 to 30 days although disease can alter this time frame. The epidermis is comprised of a number of different types of cells and the major component of these cells is the fibrous protein keratin. Many organisms that cause skin infections have special ability to utilize keratin as a food source. Skin is composed of approximately 70% water and 25% protein with the remaining 5% being composed of lipids, trace minerals, and other compounds. Due to the high level of moisture and keratin, the skin in particularly susceptible to dermatophytes that have special abilities to degrade keratin and use it as a food source. It should also be noted that the outer layer of epidermis, the corneal, is composed of dead cells rich in keratin which provide a rich food source and no antimicrobial action since they are dead.

Nails are made of modified keratin and are similar in composition to hair. Nails are about 1 to 3 mm thick and grow at a rate of between 1 to 3 mm per month taking about 6 to 12 months to completely grow out. Fingernails grow about twice as fast as toenails and the longer the finger or toe the faster the growth of the nail. The nail plate is composed of translucent keratin and is divided into three layers—the dorsal, intermediate, and ventral layers. The topmost layer is dorsal layer and it is primarily composed of soft keratin. The middle layer of the nail plate is called the intermediate layer and its cells are primarily hard keratin. The ventral layer is the bottom layer of the nail plate and it is primarily composed of soft keratin.

There are a number of different types of keratin and they are generally grouped as soft or hard keratins. Soft keratins are more prevalent in skin while hard keratins predominate in hair and nails. Approximately 80% of the keratins that comprise nails are hard keratins. Nails are relatively impervious to most compounds, which is an important protective feature. However, this protective feature also makes infections difficult to treat. The disulfide bonds of the keratin are a major factor contributing to the impermeability of nails and alteration of these bonds can significantly change the nail structure and it impermeability.

Alteration of Nail and Skin to Prevent it From Being a Food Source

It is possible to stop an infection by removing the food source of infectious organisms. If the organisms have no access to food they will be unable to reproduce and will quickly die themselves. For most skin and nail infections removing the food source means altering the keratin so that the organism can no longer utilize the keratin as a food source. Many organisms that cause skin and nail infections have specialized enzymes that can degrade keratin. However, if the keratin is crosslinked or fused by the application of means such as the use of UVC, the specialized enzymes these organisms have to degrade keratin for use as food may not be able to effectively degrade the keratin. This is due to the fact that these specialized enzymes act as a catalyst for breaking down keratin by forming a template that the keratin fits into and permits the keratin to be further broken down. If the keratin is crosslinked, or fused, it may no longer be able to fit in the template and therefore cannot be broken down and utilized by the organism as food.

Although a preferred embodiment uses the application of UVC to fuse or crosslink the keratin there are a number of other possible means that can be used to accomplish the transformation of the skin and nails so that they no longer serve as a food source. Other means include the application of other wavelengths of light, chemicals and compounds, heat, ultrasounds and other forms of energy which are known to alter structures.

Alteration of Nail and Skin to Make Produce Toxic Compounds

Keratin is a fibrous protein made up of amino acids that have particularly high amounts of sulfur. Cysteine is the primary component amino acid and its formation of disulfide bonds with adjacent strands of keratin creates a tough, fibrous matrix for the skin, nails, and hair.

Sulfur has well known antimicrobial properties and modification of the keratin in hair, nails, and skin can release sulfur and permit it to exhibit its antimicrobial effects.

Rudiger Hell of the Heidelburg Institute of Plant Sciences has identified a wide variety of sulfur based proteins that contribute to a plant's ability to resist infection. Hell notes that these proteins are termed Thionins and Defensins and defines them as "basic, low molecular weight (MW ~5000 Da) polypeptides with 10-20% cysteine residues and toxic effects to bacteria, fungi and mammals." Apparently, these compounds are toxic to infectious organisms due to their ability to disrupt membranes and other cellular processes. Applying means to keratin (which is very high in cysteine) to transform it can produce similar compounds which can have an antimicrobial effect on infectious organisms.

Skin and nails are also composed essential oils which keep them from drying out. The application of means such as UVC can alter these oils so that they are become inhibitory or toxic to organisms. There are several essential oils that are high in sulfur that have antimicrobial properties including allicin found in garlic and allyl isothiocyanate found in mustard. Applying means to alter the essential oils found in nails may also make them exhibit antimicrobial properties.

Additionally, the use of means to alter skin and nails can release sulfur which can combine with oxygen to form sulfur dioxide, another well know fungicide. Sulfur dioxide will also combine with water to form sulfurous acid which also possesses antimicrobial properties. Sulfurous acid, unlike some other forms of sulfur, can penetrate cell membranes and can inhibit the glycolic pathway thus depleting the ATP stored in the cell.

Alteration of Nail and Skin to Inhibit Organisms

Nail and skin are relatively impermeable to water and other compounds. This characteristic is a major component of skin and nails ability to resist infections and protect the body. However, altering this characteristic of the skin and nails can be a useful way to treat infections. Means such as the application of dry heat may be used to dry the skin and nails thus making the application of antimicrobial substances more effective. While dry skin and nail in and of themselves are not as healthy, this alteration of them may be carried out for a short period of time in order to treat an infection. Such drying will make the skin and nail more readily update aqueous compounds in order to rehydrate and these aqueous compounds can serve as carriers for antimicrobial compounds. In addition, many aqueous solutions are in themselves antimicrobial including sodium hypochlorite (bleach) and hydrogen peroxide.

Similarly, the skin and nails can be altered to make them less porous which is a change of state that can also be used to treat infections. Most skin and nail infections are caused by aerobic organisms, that is organisms that require free molecular oxygen to metabolize properly. If the skin and nails are altered in a manner to prevent oxygen from reaching the organism it will die or at least be much more susceptible to antimicrobial compounds. This can be accomplished by the application of an impermeable patch over the affected area. This type of patch may not be suitable by itself, however, it may be used in conjunction with the application of an inert gas such as nitrogen to prevent even small amounts of oxygen from getting to the infectious organisms.

Treatment of nail infections can also be enhanced by treating the part of the nail infection that is exposed to the air. For example, with many fungal infections there is significant debris that the end of the nail that can be removed by scraping. This exposes more of the infection and allows treatment of that exposed area. As the treatment disables the organisms it may be possible to remove additional debris, thus working the way up the nail to treat a significant portion of the infection this way. Additionally, once the debris is removed the infectious organism would be much more susceptible to treatment by soaking the toes in an antimicrobial solution (such as a solution of antifungal medication). This can be combined with the proposed method of treatment to enhance the overall effectiveness of treatment.

PREFERRED EMBODIMENT

A preferred embodiment of the invention is illustrated in FIG. 1. The invention is a method to prevent skin and nail infections and to treat existing skin and nail infections. The method of treatment uses an agent or means 10 and 12 that changes the composition of the skin 14 and nail 16 to be treated. A means 18 can be provided to prevent the alteration the other areas of the skin 20 and nails 22 that do not require treatment.

In a preferred embodiment the alteration of the skin or nail may change the skin or nail so that it no longer is a food source for the organism which causes infection. The alteration may be of the entire skin or nail or it may be the alteration of a portion of the skin or nail such as altering the skin or nail that is in direct contact with the skin or nail.

In a preferred embodiment the alteration of the skin or nail may also change the skin or nail so that the skin or nail becomes toxic to the organism which causes infection.

In a preferred embodiment the alteration of the skin or nail may also change the skin or nail so that the skin or nail in inhibitory to the organism which causes infection. The alteration of the skin or nail would change it so the organism could no longer thrive.

The electromagnetic radiation in a preferred embodiment is a specific composition of matter that is used to prevent and treat skin and nail infections. The electromagnetic radiation in the preferred embodiment consists of radiation in the UVC range (100 to 280 nm) that is capable of altering the skin or nails in a manner which either inhibits the infectious organism, is toxic to the infectious organism or which changes it so that it is not longer a source of food for the infectious organism.

In a preferred embodiment, the radiation is that which is necessary to inactivate the organisms that cause infections of the skin and nails by either inhibiting them, killing them by toxicity, or by depriving them of their source of food.

In the preferred embodiment of the invention the organisms inactivated are those that cause infections of the skin and nails. These organisms include bacteria, fungi (including dermatophytes, yeasts, molds, and non-dermatophyte molds), viruses, and other microbes. Specifically, organisms causing fungal infections of the nails, said infection being termed onychomycosis, are included in the list of organisms treated by this invention.

In the preferred embodiment, it may be necessary to irradiate the skin and nails for several times in order to completely inactivate the organisms.

In the preferred embodiment, the amount of irradiation received during one treatment may be in the approximate range of 5 to 100 mw-sec/cm2.

ALTERNATIVE EMBODIMENTS

The means to alter the skin or nails may be electromagnetic radiation in an alternative embodiment may be from UVA radiation (315 to 400 nm).

The means to alter the skin or nails may be electromagnetic radiation in an alternative embodiment may be from UVB (280 to 315 nm) radiation.

The means to alter the skin or nails may be electromagnetic radiation in an alternative embodiment may also be from the visible part of the spectrum.

The means to alter the skin or nails may be electromagnetic radiation in an alternative embodiment may be from infrared radiation.

The means to alter the skin or nails may be electromagnetic radiation in an alternative embodiment may be from radiation from a combination of visible and non-visible parts of the light spectrum.

In an alternate embodiment, the means to alter the skin or nails may be the application of heat. Heat may be applied directly by use of a heating element applied to the skin or nails or it may be applied by a source of radiation such as one generating infrared light which may heat at a distance. The heat applied may also be of a dry type designed to not only raise the temperature but also cause desiccation of the skin and nails.

In an alternate embodiment, the means to alter the skin or nails may be the application of ultrasound or other types of sound waves.

In an alternate embodiment, the means to alter the skin or nails may be the application of x-rays or other forms of radiation.

In an alternate embodiment, the means to alter the skin or nails may be the application of a compound which is not toxic to the infectious organism itself but which when applied renders the skin or nails toxic to the organism. The compound may be a chemical or a mixture of chemicals. It may also be a form of mechanical treatment such as abrasion, vibration, or heat.

In an alternate embodiment, the means to alter the skin or nails may be the application of a compound which is not inhibitory to the infectious organism itself but which when applied renders the skin or nails inhibitory to the organism. The compound may be a chemical or a mixture of chemicals. It may also be a form of mechanical treatment such as abrasion, vibration, or heat.

In an alternate embodiment, the means to alter the skin or nails may be the application of a compound which alters the skin or nail so that it is no longer a food source for the organism. The compound may be a chemical or a mixture of chemicals. It may also be a form of mechanical treatment such as abrasion, vibration, or heat.

Accordingly, it will be seen that this invention can be used to prevent and treat a wide variety of skin and nail infections. It has the following advantages over the current method of treatments for these infections:

With respect to treatment using oral medications, the invention eliminates unwanted and potentially dangerous side effects that such medications can cause.

With respect to treatment using oral medications, the invention uses a very small number of treatments (one to perhaps a dozen) to eliminate the infection while medications must be taken continuously for several months.

With respect to treatment using oral medications, the proposed treatment has the potential to be significantly less expensive than the current cost of $600 to $1200 for medicine.

With respect to treatment of nail infections using oral medications, the infection can be eliminated in much less time since the course of treatment would vary from approximately one day to one month whereas the medications must be taken from three to six months.

With respect to treatment using an induced pigment and laser to destroy an infection by heat, the invention eliminates the need for a pigment which is expensive, time consuming, and unnecessary.

With respect to treatment using an induced pigment and laser to destroy an infection by heat, the invention eliminates the need for a large amount of energy to destroy the organisms by heat which also causes damage and discomfort to the patient. The invention uses significantly less energy and thus has a much lower risk of complications.

Although the descriptions above contain many specificities, these should not be construed as limiting the scope of the invention but merely as providing illustrations of some of the presently preferred embodiments of this invention. For example, a multi-spectrum source of irradiation may be used if it has the properties necessary to alter the skin or nails.

I claim:

1. A method of preventing an infection in a patient, comprising:
   identifying an area susceptible to the infection;
   calculating an amount of energy required to prevent infection in the area;
   calculating an amount of light of about 100 nm to 400 nm that is required to achieve the amount of energy; and
   administering the amount of light to the area, wherein the intensity of the light alters the area to prevent the infection.

2. The method of claim 1, wherein administrating light comprises administering light to alter keratin in the area.

3. The method of claim 1, wherein administering light comprises administering light to alter the area to reduce food source to the infection.

4. The method of claim 1, wherein administering light comprises administering light to alter the area such that the area becomes toxic to the infection.

5. The method of claim 1, wherein administering light comprises administering light of about 100 nm to 280 nm.

6. The method of claim 5, wherein administering light comprises administering light without adding a light absorbing substance to the area.

7. The method of claim 5, further comprising applying heat to the area before administering light to the area, wherein the heat is applied using a source other than a light source.

8. The method of claim 5, further comprising altering the area before administering light to the area, wherein altering comprises applying to the area at least one of a group comprising heat, ultrasound, a chemical, and abrasion.

9. The method of claim 1, wherein administering light comprises administering light of about 280 nm to 315 nm.

10. The method of claim 1, wherein administering light comprises administering light of about 315 nm to 400 nm.

11. The method of claim 1, wherein administering light comprises administering a multispectrum light having a substantial portion of the administered light of about 100 nm to 400 nm.

12. The method of claim 1, wherein administering light comprises administering at least an amount of radiation of about 5 to 100 mw-sec/cm$^2$.

13. The method of claim 1, wherein administering light comprises administering light in multiple discrete applications such that at least an amount of radiation of about 5 to 100 mw-sec/cm$^2$ is administered during each discrete application.

14. The method of claim 1, wherein administering light comprises administering light without adding a light absorbing substance to the area.

15. The method of claim 1, further comprising applying heat to the area before administering light to the area.

16. The method of claim 15, wherein applying heat comprises applying heat with a source other than a light source.

17. The method of claim 1, further comprising altering the area before administering light to the area, wherein altering comprises applying to the area at least one of a group comprising heat, ultrasound, a chemical, and abrasion.

18. The method of claim 1, wherein the area is skin.

19. The method of claim 1, wherein the area is a nail.

20. A method for prevention or treatment of a microbial infection in a nail, comprising:
    removing at least a portion of the nail; and
    subsequently altering the nail by administering light having a wavelength substantially equal to or less than 400 nm at a time and intensity sufficient to alter the nail such that the nail inhibits the microbial infection.

21. The method of claim 20, wherein removing at least a portion of the nail comprises at least one of applying urea to the nail, abrading the nail, or excising the portion of the nail.

22. The method of claim 20, wherein administrating light comprises administering light to alter keratin in the nail.

23. The method of claim 20, wherein administering light comprises administering light to alter the nail to reduce food source to the infection.

24. The method of claim 20, wherein administering light comprises administering light to alter the nail such that the nail becomes toxic to the infection.

25. The method of claim 20, wherein administering light comprises administering light of about 100 nm to 280 nm.

26. The method of claim 25, wherein administering light comprises administering light without adding a light absorbing substance to the nail.

27. The method of claim 25, further comprising applying heat to the nail before administering light to the nail, wherein the heat is applied using a source other than a light source.

28. The method of claim 25, further comprising altering the nail before administering light to the nail, wherein altering comprises applying to the nail at least one of a group comprising heat, ultrasound, a chemical, and abrasion.

29. The method of claim 20, wherein administering light comprises administering light of about 280 nm to 315 nm.

30. The method of claim 20, wherein administering light comprises administering light of about 315 nm to 400 nm.

31. The method of claim 20, wherein administering light comprises administering a multispectrum light having a substantial portion of the administered light of about 100 nm to 400 nm.

32. The method of claim 20, wherein administering light comprises administering at least an amount of radiation of about 5 to 100 mw-sec/cm$^2$.

33. The method of claim 20, wherein administering light comprises administering light in multiple discrete applications such that at least an amount of radiation of about 5 to 100 mw-sec/cm$^2$ is administered during each discrete application.

34. The method of claim 20, wherein administering light comprises administering light without adding a light absorbing substance to the nail.

35. The method of claim 20, further comprising applying heat to the nail before administering light to the nail.

36. The method of claim 35, wherein applying heat comprises applying heat with a source other than a light source.

37. The method of claim 20, further comprising altering the nail before administering light to the nail, wherein altering comprises applying to the nail at least one of a group comprising heat, ultrasound, a chemical, and abrasion.

38. A method for prevention or treatment of a microbial infection in a nail or skin, comprising:
    applying heat to the skin or the nail; and
    subsequently altering the skin or the nail by administering light having a wavelength substantially equal to or less than 400 nm at a time and intensity sufficient to alter the skin or the nail such that the skin or the nail inhibits the microbial infection.

39. The method of claim 38, wherein administrating light comprises administering light to alter keratin in the skin or the nail.

40. The method of claim 38, wherein administering light comprises administering light to alter the skin or the nail to reduce food source to the infection.

41. The method of claim 38, wherein administering light comprises administering light to alter the skin or the nail such that the skin or the nail becomes toxic to the infection.

42. The method of claim 38, wherein administering light comprises administering light of about 100 nm to 280 nm.

43. The method of claim 42, wherein administering light comprises administering light without adding a light absorbing substance to the nail or the skin.

44. The method of claim 42, wherein applying heat comprises applying heat with a source other than a light source.

45. The method of claim 38, wherein administering light comprises administering light of about 280 nm to 315 nm.

46. The method of claim 38, wherein administering light comprises administering light of about 315 nm to 400 nm.

47. The method of claim 38, wherein administering light comprises administering a multispectrum light having a substantial portion of the administered light of about 100 nm to 400 nm.

48. The method of claim 38, wherein administering light comprises administering at least an amount of radiation of about 5 to 100 mw-sec/cm$^2$.

49. The method of claim 38, wherein administering light comprises administering light in multiple discrete applications such that at least an amount of radiation of about 5 to 100 mw-sec/cm$^2$ is administered during each discrete application.

50. The method of claim 38, wherein administering light comprises administering light without adding a light absorbing substance to the skin or the nail.

51. The method of claim 38, wherein applying heat comprises applying heat with a source other than a light source.

52. The method of claim 38, further comprising removing at least a portion of the nail by at least one of applying urea to the nail, abrading the nail, or excising the portion of the nail.

53. A method for prevention or treatment of a microbial infection in a nail or skin, comprising:
    altering the nail or the skin by applying at least one of a group comprising heat, ultrasound, a chemical, and abrasion; and
    administering light having a wavelength substantially equal to or less than 400 nm at a time and intensity sufficient to further alter the nail or the skin such that the nail or the skin inhibits the infection.

54. The method of claim 53, wherein administering light comprises administering light of about 100 nm to 280 nm.

55. The method of claim 54, wherein administering light comprises administering light without adding a light absorbing substance to the nail or the skin.

56. The method of claim 54, wherein altering the nail or the skin comprises applying heat with a source other than a light source.

57. The method of claim 53, wherein altering the nail or the skin comprises applying heat supplied by a broad spectrum light source.

58. The method of claim 53, wherein administering light comprises administering light of about 280 nm to 315 nm.

59. The method of claim 53, wherein administering light comprises administering light of about 315 nm to 400 nm.

60. The method of claim 53, wherein administering light comprises administering a multispectrum light having a substantial portion of the administered light of about 100 nm to 400 nm.

61. The method of claim 53, wherein administering light comprises administering at least an amount of radiation of about 5 to 100 mw-sec/cm$^2$.

62. The method of claim 53, wherein administering light comprises administering light in multiple discrete applications such that at least an amount of radiation of about 5 to 100 mw-sec/cm$^2$ is administered during each discrete application.

63. The method of claim 53, wherein administering light comprises administering light without adding a light absorbing substance to the skin or the nail.

64. The method of claim 53, wherein altering the nail or the skin comprises applying heat with a source other than a light source.

65. The method of claim 53, wherein altering the nail or the skin comprises soaking the skin or the nail in an antimicrobial solution.

66. The method of claim 53, wherein the microbial infection is the result of at least one of bacteria, fungi, and a virus.

67. The method of claim 53, further comprising increasing an amount of oxygen in the nail or the skin to inhibit the infection.

68. The method of claim 67, further comprising applying an impermeable patch to area surrounding the infection to decrease the amount of oxygen to inhibit the infection.

69. The method of claim 53, wherein administering light comprises administering light to further alter the skin or the nail by transforming sulfur in the skin or the nail into a compound with antimicrobial traits.

70. The method of claim 53, further comprising removing at least a portion of the nail by at least one of applying urea to the nail, abrading the nail, or excising the portion of the nail.

71. A method of preventing an infection in a patient, comprising:
    identifying an area susceptible to the infection; and
    administering an amount of light having a wavelength of substantially equal to or less that 400 nm to the area, wherein the intensity of the light alters the area to prevent the infection.

72. The method of claim 71, wherein administrating light comprises administering light to alter keratin in the area.

73. The method of claim 71, wherein administering light comprises administering light to alter the area to reduce food source to the infection.

74. The method of claim 71, wherein administering light comprises administering light to alter the area such that the area becomes toxic to the infection.

75. The method of claim 71, wherein administering light comprises administering light of about 100 nm to 280 nm.

76. The method of claim 75, wherein administering light comprises administering light without adding a light absorbing substance to the area.

77. The method of claim 75, further comprising applying heat to the area before administering light to the area, wherein the heat is applied using a source other than a light source.

78. The method of claim 75, further comprising altering the area before administering light to the area, wherein altering comprises applying to the area at least one of a group comprising heat, ultrasound, a chemical, and abrasion.

79. The method of claim 71, wherein administering light comprises administering light of about 280 nm to 315 nm.

80. The method of claim 71, wherein administering light comprises administering light of about 315 nm to 400 nm.

81. The method of claim 71, wherein administering light comprises administering a multispectrum light having a substantial portion of the administered light of about 100 nm to 400 nm.

82. The method of claim 71, wherein administering light comprises administering at least an amount of radiation of about 5 to 100 mw-sec/cm$^2$.

83. The method of claim 71, wherein administering light comprises administering light in multiple discrete applications such that at least an amount of radiation of about 5 to 100 mw-sec/cm$^2$ is administered during each discrete application.

84. The method of claim 71, wherein administering light comprises administering light without adding a light absorbing substance to the area.

85. The method of claim 71, further comprising applying heat to the area before administering light to the area.

86. The method of claim 85, wherein applying heat comprises applying heat with a source other than a light source.

87. The method of claim 71, further comprising altering the area before administering light to the area, wherein altering comprises applying to the area at least one of a group comprising heat, ultrasound, a chemical, and abrasion.

* * * * *